(12) United States Patent
Chen et al.

(10) Patent No.: US 11,826,190 B2
(45) Date of Patent: Nov. 28, 2023

(54) SYSTEM AND METHOD FOR QUANTITATIVE BLOOD VOLUME IMAGING

(71) Applicant: WISCONSIN ALUMNI RESEARCH FOUNDATION, Madison, WI (US)

(72) Inventors: Guang-Hong Chen, Madison, WI (US); Ke Li, Middleton, WI (US); Thomas Grist, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 117 days.

(21) Appl. No.: 17/375,549

(22) Filed: Jul. 14, 2021

(65) Prior Publication Data

US 2023/0026268 A1 Jan. 26, 2023

(51) Int. Cl.
*A61B 6/03* (2006.01)
*A61B 6/00* (2006.01)
*G06T 11/00* (2006.01)

(52) U.S. Cl.
CPC .............. *A61B 6/507* (2013.01); *A61B 6/032* (2013.01); *A61B 6/463* (2013.01); *G06T 11/003* (2013.01); *G06T 2211/408* (2013.01)

(58) Field of Classification Search
CPC ......... A61B 6/507; A61B 6/032; A61B 6/463; G06T 11/003; G06T 2211/408
See application file for complete search history.

(56) References Cited

U.S. PATENT DOCUMENTS

| 9,173,642 | B2 | 11/2015 | Chen | |
|---|---|---|---|---|
| 2009/0076481 | A1* | 3/2009 | Stegmann | A61K 38/1709 600/407 |
| 2022/0254016 | A1* | 8/2022 | Hoffman | A61B 6/032 |

OTHER PUBLICATIONS

Simsir et al. "Benefit of dual-layer spectral CT in emergency imaging of different organ systems", Elsevier, Clinical Radiology 75 (2020), p. 886-902 (Year: 2020).*
ACR. American College of Radiology Appropriateness Criteria®: Acute Chest Pain—Suspected Pulmonary Embolism. 2006.
Albrecht MH, Bickford MW, Nance JW, Jr., Zhang L, De Cecco CN, Wichmann JL, et al. State-of-the-Art Pulmonary CT Angiography for Acute Pulmonary Embolism. AJR Am J Roentgenol. 2017;208(3):495-504. Epub Nov. 30, 2016. doi: 10.2214/AJR.16.17202. PubMed PMID: 27897042.

(Continued)

*Primary Examiner* — David P Porta
*Assistant Examiner* — Mamadou Faye
(74) *Attorney, Agent, or Firm* — Quarles & Brady, LLP

(57) ABSTRACT

A system and method for generating reports on perfusion blood volume from computed tomography (CT) data acquired from a subject. The method includes receiving multi-faceted CT data acquired from the subject using one of a multi-energy or polychromatic CT acquisition and deriving an iodine concentration in an artery feeding a volume of interest (VOI) in the multi-faceted CT data. The method further includes determining an effective atomic number of a spatial distribution in the VOI calculating a perfused blood volume of the VOI using the iodine concentration and the effective atomic number, and generating a report of the perfused blood volume of the VOI.

16 Claims, 9 Drawing Sheets

(6 of 9 Drawing Sheet(s) Filed in Color)

(56) References Cited

OTHER PUBLICATIONS

Alvarez RE, Macovski A. Energy-selective reconstructions in X-ray computerised tomography. Physics in Medicine and Biology. 1976;21(5):733-44. doi: 10.1088/0031-9155/21/5/002.
Bauer RW, Kerl JM, Weber E, Weisser P, Korkusuz H, Lehnert T, et al. Lung perfusion analysis with dual energy CT in patients with suspected pulmonary embolism—Influence of window settings on the diagnosis of underlying pathologies of perfusion defects. Eur J Radiol. 2011;80(3):e476-e82. doi: 10.1016/j.ejrad. 2010.09.009.
Budoff MJ, Dowe D, Jollis JG, Gitter M, Sutherland J, Halamert E, et al. Diagnostic Performance of 64-Multidetector Row Coronary Computed Tomographic Angiography for Evaluation of Coronary Artery Stenosis in Individuals Without Known Coronary Artery Disease. J Am Coll Cardiol. 2008;52(21):1724-32. doi: 10.1016/j. jacc.2008.07.031. PubMed PMID: ISI:000261030900007.
Burge AJ, Freeman KD, Klapper PJ, Haramati LB. Increased diagnosis of pulmonary embolism without a corresponding decline in mortality during the CT era. Clinical Radiology. 2008;63(4):381-6. doi: 10.1016/j.crad.2007.10.004.
Chae EJ, Seo JB, Jang YM, Krauss B, Lee CW, Lee HJ, et al. Dual-Energy CT for Assessment of the Severity of Acute Pulmonary Embolism: Pulmonary Perfusion Defect Score Compared With CT Angiographic Obstruction Score and Right Ventricular/Left Ventricular Diameter Ratio. American Journal of Roentgenology. 2010;194(3):604-10. doi: 10.2214/ajr.09.2681.
Devaraj A, Sayer C, Sheard S, Grubnic S, Nair A, Vlahos I. Diagnosing acute pulmonary embolism with computed tomography: imaging update. J Thorac Imaging. 2015;30(3):176-92. Epub Mar. 27, 2015. doi: 10.1097/RTI.0000000000000146. PubMed PMID: 25811355.
Di Nisio M, van Es N, Büller HR. Deep vein thrombosis and pulmonary embolism. The Lancet. 2016;388(10063):3060-73. doi: 10.1016/s0140-6736(16)30514-1.
Einstein AJ, Henzlova MJ, Rajagopalan S. Estimating Risk of Cancer Associated With Radiation Exposure From 64-Slice Computed Tomography Coronary Angiography. JAMA. 2007;298(3):317-23.
Hartmann IJ, Wittenberg R, Schaefer-Prokop C. Imaging of acute pulmonary embolism using multi-detector CT angiography: an update on imaging technique and interpretation. Eur J Radiol. 2010;74(1):40-9. Epub Mar. 17, 2010. doi: 10.1016/j.ejrad.2010. 02.007. PubMed PMID: 20227213.
Hubbell JH, Seltze SM. X-Ray Mass Attenuation Coefficients. NIST Standard Reference Database 126. 2004. doi: https://dx.doi.org/10. 18434/T4D01F.
Im DJ, Hur J, Han KH, Lee HJ, Kim YJ, Kwon W, et al. Acute Pulmonary Embolism: Retrospective Cohort Study of the Predictive Value of Perfusion Defect Volume Measured With Dual-Energy CT. AJR Am J Roentgenol. 2017;209(5):1015-22. Epub Sep. 13, 2017. doi: 10.2214/AJR.17.17815. PubMed PMID: 28898127.
Kim YS. Human Tissues—Chemical Composition and Photon Dosimetry Data. Radiat Res. 1974;57(1):38-45. doi: Doi 10.2307/3573753. PubMed PMID: ISI:A1974S010500004.
Ko JP, Brandman S, Stember J, Naidich DP. Dual-energy computed tomography: concepts, performance, and thoracic applications. Journal of thoracic imaging. 2012;27(1):7-22.
Kong WF, Wang YT, Yin LL, Pu H, Tao KY. Clinical risk stratification of acute pulmonary embolism: comparing the usefulness of CTA obstruction score and pulmonary perfusion defect score with dual-energy CT. Int J Cardiovasc Imaging. 2017;33(12):2039-47. Epub Jun. 15, 2017. doi: 10.1007/s10554-017-1188-x. PubMed PMID: 28612276.
Kunihiro Y, Okada M, Matsunaga N. Evaluation of a proper cutoff value on quantitative dual-energy perfusion CT for the assessment of acute pulmonary thromboembolism. Acta Radiol. 2017;58(9):1061-7. Epub Feb. 2, 2017. doi: 10.1177/0284185116683577. PubMed PMID: 28142251.
Lehmann LA, Alvarez RE, Macovski A, Brody WR, Pelc NJ, Riederer SJ, et al. Generalized image combinations in dual KVP digital radiography. Medical physics. 1981;8(5):659-67. doi: 10.1118/1.595025.
Lu GM, Zhao YE, Zhang LJ, Schoepf UJ. Dual-energy CT of the lung. American Journal of Roentgenology. 2012;199 (5_supplement):S40-S53.
McCollough CH, Primak AN, Saba O, Bruder H, Stierstorfer K, Raupach R, et al. Dose performance of a 64-channel dual-source CT scanner. Radiology. 2007;243(3):775-84. PubMed PMID: 17446525.
Miller JM, Rochitte CE, Dewey M, Arbab-Zadeh A, Niinuma H, Gottlieb I, et al. Diagnostic Performance of Coronary Angiography by 64-Row CT. New England Journal of Medicine. 2008;359(22):2324-36. doi: Doi 10.1056/Nejmoa0806576. PubMed PMID: ISI:000261270300004.
Moore AJE, Wachsmann J, Chamarthy MR, Panjikaran L, Tanabe Y, Rajiah P. Imaging of acute pulmonary embolism: an update. Cardiovasc Diagn Ther. 2018;8(3):225-43. Epub Jul. 31, 2018. doi: 10.21037/cdt.2017.12.01. PubMed PMID: 30057872; PubMed Central PMCID: PMC6039809.
Murty RC. Effective Atomic Numbers of Heterogeneous Materials. Nature. 1965;207(4995):398-&. doi: Doi 10.1038/207398a0. PubMed PMID: ISI:A19656646900047.
Okada M, Kunihiro Y, Nakashima Y, Nomura T, Kudomi S, Yonezawa T, et al. Added value of lung perfused blood volume images using dual-energy CT for assessment of acute pulmonary embolism. European Journal of Radiology. 2015;84(1):172-7. doi: 10.1016/j.ejrad.2014.09.009. PubMed PMID: ISI:000346386100023.
Phillips JJ, Straiton J, Staff RT. Planar and SPECT ventilation/perfusion imaging and computed tomography for the diagnosis of pulmonary embolism: A systematic review and meta-analysis of the literature, and cost and dose comparison. Eur J Radiol. 2015;84(7):1392-400. Epub Apr. 15, 2015. doi: 10.1016/j.ejrad.2015.03.013. PubMed PMID: 25868674.
Pontana F, Faivre JB, Remy-Jardin M, Flohr T, Schmidt B, Tacelli N, et al. Lung perfusion with dual-energy multidetector-row CT (MDCT): feasibility for the evaluation of acute pulmonary embolism in 117 consecutive patients. Acad Radiol. 2008;15(12):1494-504. Epub Nov. 13, 2008. doi: 10.1016/j.acra.2008.05.018. PubMed PMID: 19000866.
Rajiah P. Dual-Energy Computed Tomography in Thoracic Imaging—Current Practices and Utility: Survey of the Society of Thoracic Radiology. J Thorac Imaging. 2020;35(2).
Rassouli N, Etesami M, Dhanantwari A, Rajiah P. Detector-based spectral CT with a novel dual-layer technology: principles and applications. Insights Imaging. 2017;8(6):589-98. Epub Oct. 8, 2017. doi: 10.1007/s13244-017-0571-4. PubMed PMID: 28986761; PubMed Central PMCID: PMC5707218.
Redberg RF, Walsh J. Pay now, benefits may follow—the case of cardiac computed tomographic angiography. N Engl J Med. 2008;359(22):2309-11. Epub Nov. 29, 2008. doi: 10.1056/NEJMp0805920. PubMed PMID: 19038877.
Remy-Jardin M, Pistolesi M, Goodman LR, Gefter WB, Gottschalk A, Mayo JR, et al. Management of suspected acute pulmonary embolism in the era of CT angiography: a statement from the Fleischner Society. Radiology. 2007;245(2):315-29. Epub Sep. 13, 2007. doi: 10.1148/radiol.2452070397. PubMed PMID: 17848685.
Renapurkar RD, Bolen MA, Shrikanthan S, Bullen J, Karim W, Primak A, et al. Comparative assessment of qualitative and quantitative perfusion with dual-energy CT and planar and SPECT-CT V/Q scanning in patients with chronic thromboembolic pulmonary hypertension. Cardiovasc Diagn Ther. 2018;8(4):414-22. Epub Sep. 15, 2018. doi: 10.21037/cdt.2018.05.07. PubMed PMID: 30214856; PubMed Central PMCID: PMC6129841.
Sakamoto A, Sakamoto I, Nagayama H, Koike H, Sueyoshi E, Uetani M. Quantification of lung perfusion blood volume with dual-energy CT: assessment of the severity of acute pulmonary thromboembolism. AJR Am J Roentgenol. 2014;203(2):287-91. Epub Jul. 24, 2014. doi: 10.2214/AJR.13.11586. PubMed PMID: 25055261.
Spiers FW. Effective Atomic Number and Energy Absorption in Tissues. Brit J Radiol. 1946;19(218):52-63. doi: Doi 10.1259/0007-1285-19-218-52. PubMed PMID: ISI:A1946UD67300002.

(56) References Cited

OTHER PUBLICATIONS

Stolzmann P, Scheffel H, Schertler T, Frauenfelder T, Leschka S, Husmann L, et al. Radiation dose estimates in dual-source computed tomography coronary angiography. Eur Radiol. 2007. PubMed PMID: 17909816.

Surdarski et al., "Pulmonary Perfusion Imaging with CT," Radiology Key, Ultrasonography, Jul. 8, 2020.

Wildberger JE, Schoepf UJ, Mahnken AH, Herzog P, Ditt H, Niethammer MU, et al. Approaches to CT perfusion imaging in pulmonary embolism. Semin Roentgenol. 2005;40(1):64-73. Epub Mar. 1, 2005. PubMed PMID: 15732562.

Wittram C, Maher MM, Yoo AJ, Kalra MK, Shepard JAO, McLoud TC. CT angiography of pulmonary embolism: Diagnostic criteria and causes of misdiagnosis. Radiographics. 2004;24(5):1219-38. doi: Doi 10.1148/Rg.245045008. PubMed PMID: ISI:000223807800001.

Yang NC, Leichner PK, Hawkins WG. Effective atomic numbers for low-energy total photon interactions in human tissues. Medical Physics. 1987;14(5):759-66. doi: https://doi.org/10.1118/1.596000.

Zhang L-J, Chai X, Wu S-Y, Zhao Y-E, Hu X-B, Hu Y-X, et al. Detection of pulmonary embolism by dual energy CT: correlation with perfusion scintigraphy and histopathological findings in rabbits. European Radiology. 2009;19(12):2844.

Zhang L-J, Zhao Y-E, Wu S-Y, Yeh BM, Zhou C-S, Hu X-B, et al. Pulmonary embolism detection with dual-energy CT: experimental study of dual-source CT in rabbits. Radiology. 2009;252(1):61-70.

\* cited by examiner

SYSTEM AND METHOD FOR QUANTITATIVE BLOOD VOLUME IMAGING

STATEMENT REGARDING FEDERALLY SPONSORED RESEARCH

This invention was made with government support under EB021183 and EB020521 awarded by the National Institutes of Health. The government has certain rights in the invention.

CROSS-REFERENCE TO RELATED APPLICATIONS

N/A

BACKGROUND

The present disclosure relates to systems and methods for creating quantitative blood volume images. More particularly, the disclosure relates to systems and methods for creating images that include quantitative, including absolute, perfusion blood volume, for example, of the lung, using computed tomography data.

Venous thromboembolism is a major global health concern and an economic burden with approximately 10 million cases occurring each year and a high lifetime risk of 8% after 45 years of age. Pulmonary embolism (PE) is a venous thromboembolic event associated with high morbidity and mortality. Currently, pulmonary CT angiography (CTA) is the preferred imaging modality for evaluating patients with clinically suspected acute PE. Pulmonary CTA can also be used for the evaluation of other pulmonary thromboembolic diseases such as chronic PE and chronic thromboembolic pulmonary hypertension (CTEPH). Pulmonary emboli often manifest as partial or complete intraluminal pulmonary vessel filling defects on pulmonary CTA images and each defect usually presents a sharp interface with the iodinated contrast. However, these radiological features are not specific to pulmonary emboli and can also result from a number of other pathological factors (e.g., the presence of a mucus plug or perivascular edema) and anatomical factors (e.g., vascular bifurcations, misidentification of pulmonary veins, etc.), all of which can generate PE-mimicking filling defects on pulmonary CTA images.

In addition to these challenges to using CTA in these clinical settings, the success rate and diagnostic accuracy of anatomic imaging with pulmonary CTA drop as the vessel size decreases to the subsegmental level. Furthermore, pulmonary CTA only provides anatomic imaging of pulmonary vessels and does not provide a direct assessment of the impact of PE on lung parenchymal perfusion. Pulmonary CTA also cannot directly provide prognostic biomarkers of hemodynamic compromise nor identify patients at risk for fatal or other adverse events. The incapability to demonstrate parenchymal perfusion abnormalities remains an important limitation of CTA-based evaluation of pulmonary thromboembolic diseases.

As an alternative to pulmonary CTA, lung ventilation/perfusion (V/Q) scintigraphy, and single photon emission computed tomography (SPECT) are also used to evaluate pulmonary thromboembolic diseases. For patients with suspected CTEPH or chronic PE, the selection between CTA and nuclear medicine imaging often creates a diagnostic dilemma. That is, CTA provides direct imaging of the embolus itself without parenchymal perfusion information, while nuclear medicine imaging provides functional information without direct proof of emboli. To extricate physicians from this dilemma, patients with suspected CTEPH may need to receive both CTA and nuclear medicine lung imaging, which increases both the overall healthcare cost and the ionizing radiation dose to patients. As a result, there is a compelling unmet clinical need to develop new or further ways to perform pulmonary vessel morphological assessment and parenchymal perfusion assessment without applying separate CT and nuclear medicine scans to the same patient.

Towards providing a "one-stop-shop" solution to morphological and functional lung imaging, prior studies have investigated the use of dynamic CT imaging to extract pulmonary perfusion information. However, this approach has not been clinically accepted due to concerns regarding radiation dose. For example, the effective dose of dynamic chest CT is approximately 7 mSv, compared to 2 mSv for a typical static pulmonary CTA scan. Another strategy employed is to use static dual energy CT (DECT) or multi-energy CT (MECT) that does not require a prolonged breath-hold or a significant increase in radiation dose. A DECT scan generates the so-called iodine basis images that can be used to define the relative pulmonary perfusion blood volume (rPBV) maps to depict the location and pattern of pulmonary perfusion defects. For a given pulmonary embolus identified on CTA images, the addition of rPBV maps can assist physicians in estimating the probability and severity of tissue damage, while providing a prognosis and risk stratification in patients presenting with pulmonary thromboembolic diseases, including typical presentations and those associated with alternate diagnoses, such as COVID-19 pneumonia.

However, as shown by a recent survey conducted by the Society of Thoracic Radiology (Rajiah P. Dual-Energy Computed Tomography in Thoracic Imaging—Current Practices and Utility: Survey of the Society of Thoracic Radiology. J Thorac Imaging. 2020; 35(2), iodine basis image-based pulmonary perfusion imaging remains underutilized in clinical practice due to several important limitations. The first important limitation of the iodine basis image is that its signal does not necessarily reflect the magnitude of the pulmonary blood pool, for example, because non-iodine materials, especially those with large mass densities, can also contribute to the iodine basis image. Consequently, a region with perfusion defects can appear to be normal in iodine basis images, if other high density clinical conditions such as consolidation, ground glass opacity, or atelectasis are present. The second limitation lies in the fact that the iodine image-based pulmonary perfusion evaluation method can only provide a relative measurement of perfusion defects—the resulting images or reports are not absolutely quantitative, but are only relative measures in the context of that imaging study. In fact, physicians heavily rely on comparing the iodine intensity across different lung lobes to identify regional perfusion defects. Due to this relative assessment nature, literature on DECT pulmonary perfusion imaging rarely reports the units of the pulmonary perfusion maps. This limitation poses a challenge in diagnosing systematic pulmonary defects.

Therefore, it would be desirable to provide systems and methods for assisting clinicians in assessing pulmonary embolus.

SUMMARY OF THE INVENTION

The present invention overcomes the aforementioned drawbacks by providing a system and method for quantitative or non-relative blood volume imaging using computed tomography. The systems and methods provided herein facilitate the use of computed tomography to elicit atomic-number-based quantitation of blood volume. The systems and methods provided can be used for the creation of quantitative blood volume images or maps, for example, that can be used to facilitate the quantification of pulmonary perfusion defects.

In accordance with one aspect of the invention, a system is provided for determining perfusion blood volume from computed tomography (CT) data acquired from a subject. The system includes a storage medium having multi-faceted CT data stored thereon that includes data acquired with at least one of a multi-energy x-ray source or a polychromatic x-ray source. The system also includes a computer system configured to receive the multi-faceted CT data from the storage medium and derive an iodine concentration in an artery feeding a volume of interest (VOI) in the multi-faceted CT data. The computer system is further configured to determine an effective atomic number of a spatial distribution in the VOI, calculate a perfused blood volume of the VOI using the iodine concentration and the effective atomic number, and generate a report of the perfused blood volume of the VOI. The system further includes a display configured to display the report, including the perfused blood volume of the VOI.

In accordance with yet another aspect of the invention, a method is provided for generating reports on perfusion blood volume from computed tomography (CT) data acquired from a subject. The method includes receiving multi-faceted CT data acquired from the subject using one of a multi-energy or polychromatic CT acquisition and deriving an iodine concentration in an artery feeding a volume of interest (VOI) in the multi-faceted CT data. The method further includes determining an effective atomic number of a spatial distribution in the VOI, calculating a perfused blood volume of the VOI using the iodine concentration and the effective atomic number, and generating a report of the perfused blood volume of the VOI.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or patent application file contains at least one drawing executed in color. Copies of this patent or patent application publication with color drawings drawing(s) will be provided by the Office upon request and payment of the necessary fee.

DETAILED DESCRIPTION OF THE INVENTION

Figure 1:
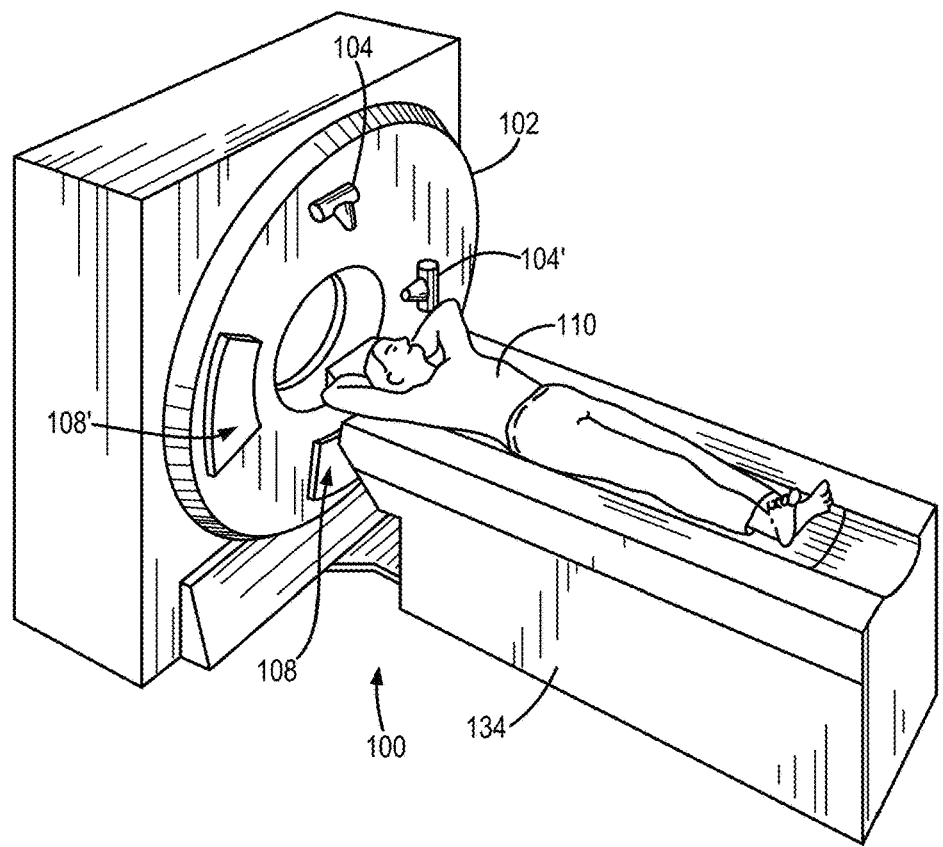
FIG. 1 is a perspective view of a dual-energy, x-ray, computed tomography (CT) system configured in accordance with the present disclosure.

Dual or multi-energy computed tomography (CT) imaging system provide the ability to image a subject using more than one x-ray energy spectra. Many such imaging systems use specialized hardware to image at more than one energy level in a given acquisition. For example, turning to FIGS. 1 and 2, a traditional dual-energy, CT system is illustrated, such as is commercially available. In particular, a dual-energy CT imaging system 100 includes a gantry 102 having a one or more x-ray sources 104, 104' that project a fan beam or cone beam of x-rays 106, 106' toward a detector array 108, 108' on the opposite side of the gantry 102. As illustrated, there may be a single source 104 or two or more source 104'. That is, some commercially-available, dual-energy systems employ a single source 104 that is switched between high and low energies and other commercially-available, dual-energy systems employ two dedicated sources 104, 104' that are used to generate the high and low energies. That is, historically, to enable dual-energy CT imaging, one either required two-tube-two-detector technique, or one has to have special x-ray generator, tube, and also detector to enable fast kV switching acquisition technique, or a special sandwich detector or photon counting detector to enable energy resolving x-ray detections. The detector array 108, 108' is formed by a number of detector elements 112 that together sense the projected x-rays that pass through a medical patient 110. Each detector element 112, 112' produces an electrical signal in response to receiving photon or bunches of photons.

During a scan to acquire x-ray projection data, the gantry 102 and the components mounted thereon rotate about a center of rotation 114 located within the patient 110 to acquire attenuation data. The rotation of the gantry and the operation of the x-ray source(s) 104 (104') are governed by a control system 116 of the CT system. The control system 116 includes an x-ray controller 22 that provides power and timing signals to the x-ray source(s) 104 (104') and a gantry motor controller 120 that controls the rotational speed and position of the gantry 102. A data acquisition system (DAS) 24 in the control system 116 samples analog data from detector elements 112 and converts the data to digital signals for subsequent processing. An image reconstructor 25, receives sampled and digitized x-ray data from the DAS 122 and performs high speed image reconstruction. The reconstructed image is applied as an input to a computer 124 which stores the image in a mass storage device 126.

The computer 124 also receives commands and scanning parameters from an operator via a console 128 that has a keyboard. An associated display 130 allows the operator to observe the reconstructed image and other data from the computer 124. The operator supplied commands and parameters are used by the computer 124 to provide control signals and information to the DAS 122, the x-ray controller 118, and the gantry motor controller 23. In addition, the computer 124 operates a table motor controller 132 that controls a motorized table 134 to position the patient 110 in the gantry 102.

Whether employing two, dedicated sources 104, 104' or switching operation of a single source 104 between two tube potentials, these dual- or multi-energy imaging systems are generally of higher cost and complexity than traditional imaging systems due to the need for specialized hardware and software, such as additional sources 104', detector arrays 108', and communications and software for processing feedback from different energy levels from individual detector elements 112, 112'.

Figure 2:
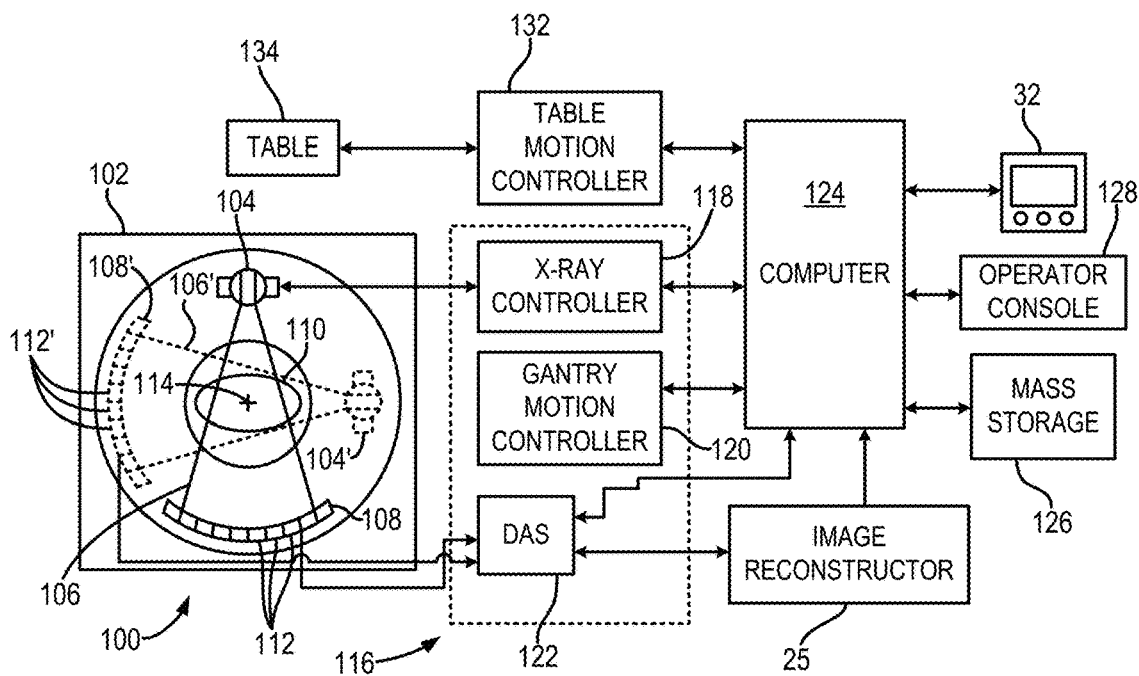
FIG. 2 is a block diagram of the traditional, dual-energy, x-ray, CT system of FIG. 1.
Figure 3:
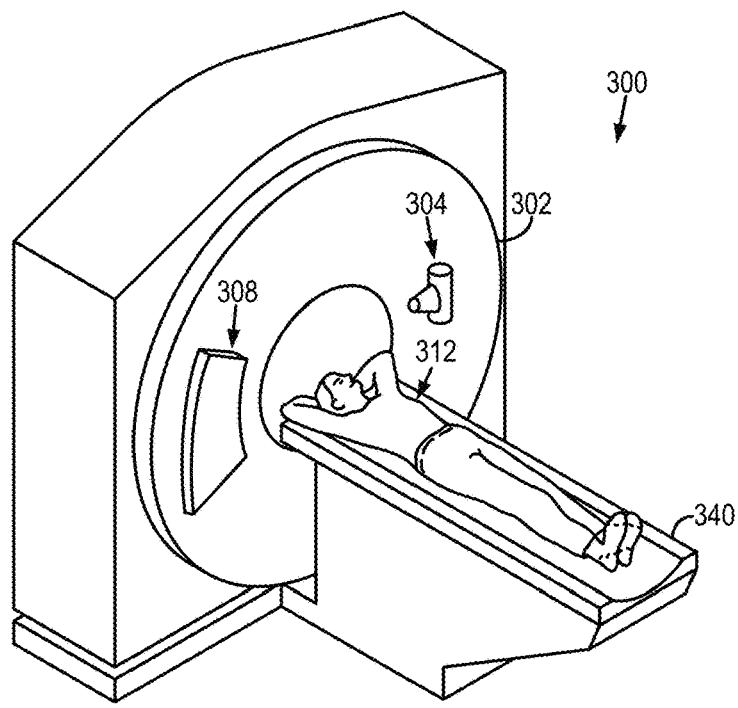
FIG. 3 a perspective view of a polychromatic, x-ray, CT system configured in accordance with the present disclosure.
Figure 4:
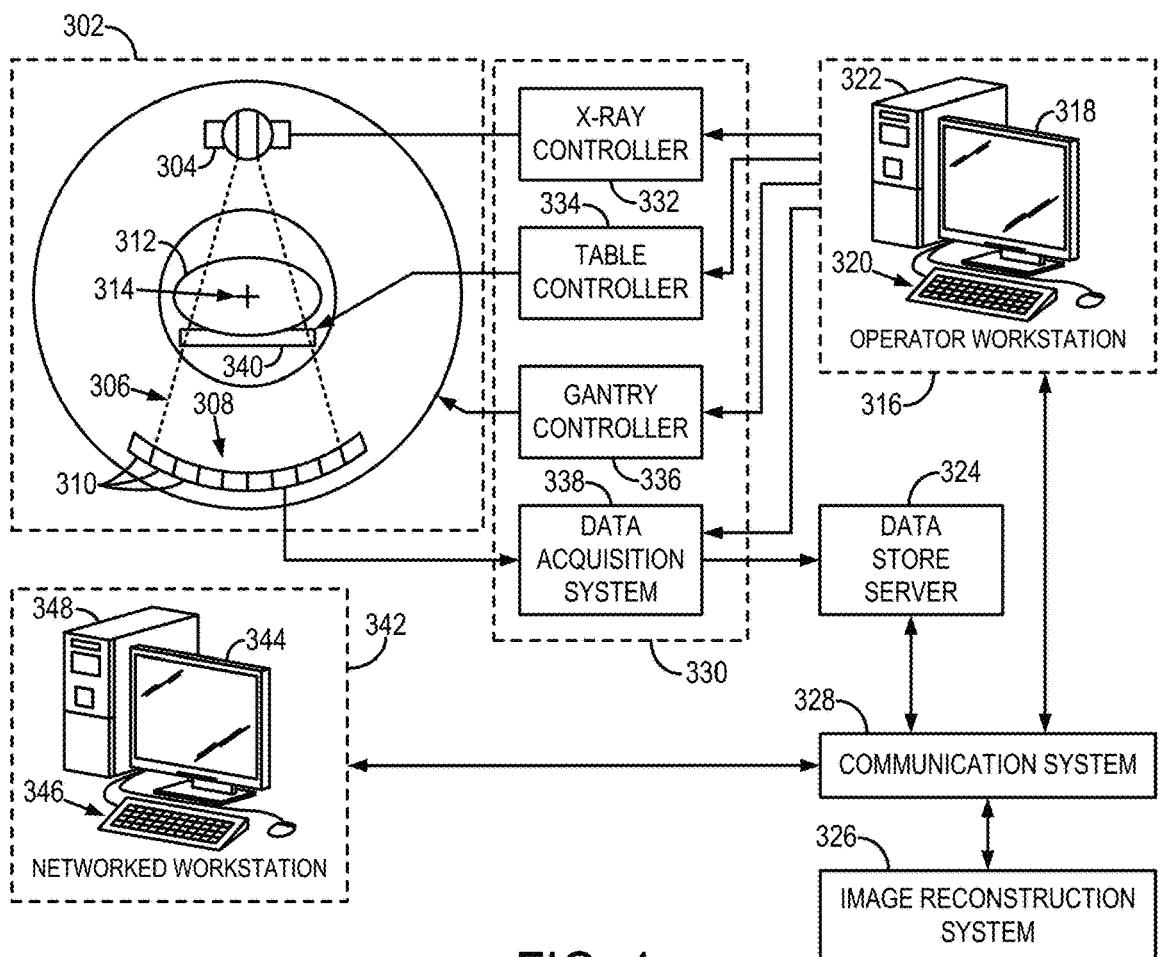
FIG. 4 is a block diagram of the polychromatic, x-ray, CT system of FIG. 3.

Referring particularly now to FIGS. 3 and 4, more-recent technological advances have allowed a "traditional" (non-multi- or non-dual-energy) CT imaging system 300 has been empowered to yield data that was historically available only using the systems of FIGS. 1 and 2. The CT system includes 300 a gantry 302, to which one, polychromatic, x-ray source 304 is coupled. As fully explained in U.S. Pat. No. 9,173, 624, which is incorporated herein by reference in its entirety, energy information associated with using a polychromatic x-ray source with single spectrum was viewed as undesirable because the polychromatic-nature of the x-ray source is contrary to the objective of single-energy imaging. However, the present invention can further unlock and utilize such information that was traditionally not available to, thereby, provide multi-energy imaging information without the cost or complexity of traditional multi-energy systems or the added patient dose required by such traditional, multi-energy systems.

The x-ray source 304 projects a polychromatic x-ray beam 306, which may be a fan-beam or cone-beam of x-rays, towards a detector array 308 on the opposite side of the gantry 302. The detector array 308 includes a number of x-ray detector elements 310. Together, the x-ray detector elements 310 sense the projected x-rays 306 that pass through a subject 312, such as a medical patient or an object undergoing examination, that is positioned in the CT system 300. Each x-ray detector element 310 produces an electrical signal in response to an impinging polychromatic x-ray beam and, hence, the attenuation of the beam as it passes through the subject 312. In some configurations, each x-ray detector 310 may be capable of counting the number of x-ray photons that impinge upon the detector 310. During a scan to acquire x-ray projection data, the gantry 302 and the components mounted thereon rotate about a center of rotation 314 located within the CT system 300.

The CT system 300 also includes an operator workstation 316, which typically includes a display 318; one or more input devices 320, such as a keyboard and mouse; and a computer processor 322. The computer processor 322 may include a commercially available programmable machine running a commercially available operating system. The operator workstation 316 provides the operator interface that enables scanning control parameters to be entered into the CT system 300. In general, the operator workstation 316 is in communication with a data store server 324 and an image reconstruction system 326. By way of example, the operator workstation 316, data store sever 324, and image reconstruction system 326 may be connected via a communication system 328, which may include any suitable network connection, whether wired, wireless, or a combination of both. As an example, the communication system 328 may include both proprietary or dedicated networks, as well as open networks, such as the internet.

The operator workstation 316 is also in communication with a control system 330 that controls operation of the CT system 300. The control system 330 generally includes an x-ray controller 332, a table controller 334, a gantry controller 336, and a data acquisition system 338. The x-ray controller 332 provides power and timing signals to the x-ray source 304 and the gantry controller 336 controls the rotational speed and position of the gantry 302. The table controller 334 controls a table 340 to position the subject 312 in the gantry 302 of the CT system 300.

The DAS 338 samples data from the detector elements 310 and converts the data to digital signals for subsequent processing. For instance, digitized x-ray data is communicated from the DAS 338 to the data store server 324. The image reconstruction system 326 then retrieves the x-ray data from the data store server 324 and reconstructs an image therefrom. The image reconstruction system 326 may include a commercially available computer processor, or may be a highly parallel computer architecture, such as a system that includes multiple-core processors and massively parallel, high-density computing devices. Optionally, image reconstruction can also be performed on the processor 322 in the operator workstation 316. Reconstructed images can then be communicated back to the data store server 324 for storage or to the operator workstation 316 to be displayed to the operator or clinician.

The CT system 300 may also include one or more networked workstations 342. By way of example, a networked workstation 342 may include a display 344; one or more input devices 346, such as a keyboard and mouse; and a processor 348. The networked workstation 342 may be located within the same facility as the operator workstation 316, or in a different facility, such as a different healthcare institution or clinic.

The networked workstation 342, whether within the same facility or in a different facility as the operator workstation 316, may gain remote access to the data store server 324 and/or the image reconstruction system 326 via the communication system 328. Accordingly, multiple networked workstations 342 may have access to the data store server 324 and/or image reconstruction system 326. In this manner, x-ray data, reconstructed images, or other data may be exchanged between the data store server 324, the image reconstruction system 326, and the networked workstations 342, such that the data or images may be remotely processed by a networked workstation 342. This data may be exchanged in any suitable format, such as in accordance with the transmission control protocol ("TCP"), the internet protocol ("IP"), or other known or suitable protocols.

Using any of the systems described above or similar systems, the present disclosure provides systems and methods to yield clinical insights not previously available, even using the systems described above. For example, in one aspect of the disclosure, a framework is provided to derive quantitative pulmonary perfusion blood volume (PBV) maps from dual-energy, multi-energy, or poly-chromatic datasets or images, referred to herein as multi-facet datasets or multi-facet images. Multi-facet datasets or images, for example, have a measured x-ray attenuation coefficient μ. The systems and methods provided herein overcome the current limitations of iodine image-based perfusion assessment and can, optionally, be used to achieve simultaneous functional and anatomical lung imaging. As will be described, quantitative and absolute PBV measurements can be determined from multi-facet data or images using the systems and methods provided herein, for example, by using a local effective atomic number distribution and, thus, can provide an intrinsic absolute quantification of the perfused blood pool.

Figure 5:
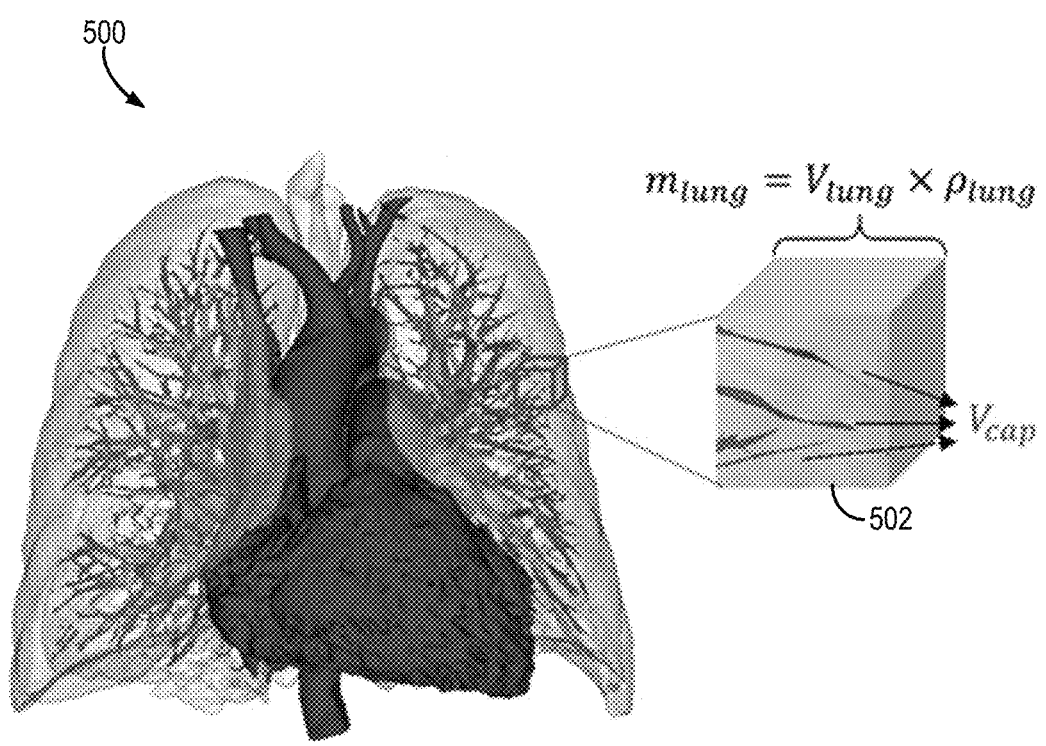
FIG. 5 is a graphic illustration of a selected volume of interest showing a pulmonary perfused blood volume (PBV).

Referring to FIG. 5, an illustration of the concept of pulmonary perfused blood volume (PBV) 500 is provided. For a given volume-of-interest (VOI) 502 in the lung parenchyma, its PBV is given by the ratio between the volume occupied by the capillaries ($V_{cap}$) and the mass of the lung tissue in the VOI ($m_{lung}$). $m_{lung} = V_{lung}\, \rho_{lung}$, where $V_{lung}$ and $\rho_{lung}$ are the volume and density of the lung tissue in the VOI, respectively PBV is the blood volume perfused into a unit mass of lung tissue in a small volume around location x:

$$PBV(x) = \frac{V_{cap}(x)}{m_{lung}(x)}; \tag{1}$$

where $V_{cap}(x)$ denotes the volume of the capillary bed within a VOI at a location x in the lung and $m_{lung}(X)$ denotes the mass of the lung tissue in the VOI.

In practice, it is difficult to directly measure the volume of the capillary bed within a VOI due to the limited spatial resolution of CT. Therefore, the present disclosure recognizes that PBV can be determined from other directly measurable quantities in an image volume.

Using the relationship between mass, mass density, and volume, the PBV formula in Equation (1) can be recast to:

$$PBV(x) = \frac{1}{r_{lung}(x)} \frac{V_{cap}(x)}{V_{lung}(x)}; \tag{2}$$

where $$\frac{V_{cap}(x)}{V_{lung}(x)}$$

denotes the volume fraction of the capillary bed in the VOI at x. When the iodinated contrast medium is injected into the blood stream and the pulmonary capillary bed is perfused with the iodinated blood, the mass of iodine that flows into the VOI in the lung is the same mass of iodine in the capillary bed, namely:

$$m_{I,cap} = m_{I,VOI} \tag{3}$$

However, the mass of iodine in the capillary bed is given by the product of iodine concentration in the input artery, $\rho_{I_o}$, and the volume of the capillary bed in the VOI, $V_{cap}(x)$, such that:

$$m_{I,cap} = \rho_{I_o} V_{cap}(x) = m_{I,VOI} \tag{4}$$

Therefore, the averaged concentration of iodinated blood in the lung tissue VOI is given by:

$$\rho_I(x) = \frac{m_{I,VOI}}{V_{lung}(x)} = \frac{\rho_{I_o} V_{cap}(x)}{V_{lung}(x)}; \tag{5}$$

This formula can be re-written to obtain the ratio of the capillary bed in the lung tissue VOI as the ratio between the iodine concentration in the VOI and the iodine concentration in the input artery as follows:

$$\frac{V_{cap}(x)}{V_{lung}(x)} = \frac{\rho_I(x)}{\rho_{I_0}}; \tag{6}$$

By combining Equations (2) and (6), using the mass conservation principle, the following equation is obtained for PBV:

$$PBV(x) = \frac{1}{r_{lung}(x)} \frac{r_I(x)}{r_{I_0}}; \tag{7}$$

where $\rho_{I_o}$ is the iodine concentration in the feeding pulmonary artery and $\rho_I(x)$ is the iodine concentration in the VOI. The key difference between Equation (1) and Equation (7) is that all three quantities in Equation (7) are now experimentally measurable using imaging methods. Therefore, Equation (7) provides an imaging physics foundation to experimentally determine pulmonary perfused blood volume.

To determine the iodine concentrations and mass density of lung tissue in Equation (7), multi-facet datasets or images can be used. To estimate $\rho_I(x)$, multi-facet datasets or images, with a measured x-ray attenuation coefficient μ, can be decomposed into, for example, two material bases as:

$$\mu(x, E) = a_I(x)\left(\frac{\mu}{\rho}\right)_I(E) + a_w(x)\left(\frac{\mu}{\rho}\right)_w(E); \tag{8}$$

or three material bases as:

$$\mu(x, E) = a_I(x)\left(\frac{\mu}{\rho}\right)_I(E) + a_w(x)\left(\frac{\mu}{\rho}\right)_w(E) + a_{air}(x)\left(\frac{\mu}{\rho}\right)_{air}(E); \tag{9}$$

where E denotes the x-ray energy, and $$\left(\frac{\mu}{\rho}\right)_I, \left(\frac{\mu}{\rho}\right)_w, \text{ and } \left(\frac{\mu}{\rho}\right)_{air}$$

denote the mass attenuation coefficient of pure iodine, water, and air, respectively. The material "water" can also be replaced by a "standard soft tissue material", but the overall working principle remains the same.

Conventional measurements using iodine basis images provide only "relative PBV" (rPBV) and not PBV, even when it says otherwise. That is, a standard iodine basis image, $a_I(x)$ presents rPBV because it is be equivalent to $\rho_I(x)$ in Equation (7). In other words, while the iodine basis image is assumed to be linearly proportional to PBV, in reality, this assumption is not supported by imaging physics.

Thus, as will be demonstrated, when traditional or conventional CT data or images (non-multi-faceted CT datasets or images) are used to determine what is presented as "PBV," this is a misnomer. When traditional or conventional CT data or images (non-multi-faceted CT datasets or images) are used to determine "PBV," only rPBV is determined, as will be shown.

First, the iodine basis image, $a_I(x)$, is not the same as the iodine concentration distribution, $\rho_I(x)$, despite the fact that the physical unit of $a_I(x)$ is the same as that of $\rho_I(x)$ (e.g., mg/ml). The actual physical meaning of $a_I(x)$ and $a_w(x)$ are given by the following formulae:

$$a_I(x) = \frac{\rho_e(x)}{N_a\left(\frac{Z}{A}\right)_I} \frac{Z^\beta_{eff}(x) - Z^\beta_w}{Z^\beta_I - Z^\beta_w}; \tag{10}$$

$$a_w(x) = \frac{\rho_e(x)}{N_a\left(\frac{Z}{A}\right)_w} \frac{Z^\beta_{eff}(x) - Z^\beta_I}{Z^\beta_w - Z^\beta_I}; \tag{11}$$

where $\beta$ is an energy- and material-independent numerical constant, $N_a$ is the Avogadro constant, $\rho_e(x)$ denotes the electron density of the VOI, A denotes the atomic mass number, Z denotes the atomic number, and which $Z_{eff}$ is defined as $$Z_{eff} = \left[\sum_{j=1}^n f_i Z_i^\beta\right]^{\frac{1}{\beta}},$$

where $Z_i$ is the atomic number of the $i^{th}$ constituent material in the VOI at x, and $f_i$ is the fraction of electrons associated with the $i^{th}$ material. For example, $Z_I(=53)$ and $Z_w(=7.4)$ are the atomic numbers of pure iodine and water, respectively.

Thus, $a_I(x)$ equals $\rho_I(x)$ only under the assumption that the VOI is entirely composed of iodine and water. That is, under this very-special condition:

$$Z_{eff}^\beta(x) = f_I(x)Z_I^\beta + [1 - f_I(x)]Z_w^\beta = f_I(x)(Z_I^\beta - Z_w^\beta) + Z_w^\beta \tag{12}$$

where $f_I$ denotes the fraction of electrons coming from the iodine atoms. Under the condition in Equation (12), the formula of $a_I(x)$ in Equation (10) can be written as:

$$a_I(x) = \frac{\rho_e(x)}{N_a\left(\frac{Z}{A}\right)_I} \frac{f_I(x)(Z^\beta_{eff}(x) - Z^\beta_w) + Z^\beta_w - Z^\beta_w}{Z^\beta_I - Z^\beta_w} = \tag{13}$$

$$\frac{\rho_e(x) f_I(x)}{N_a\left(\frac{Z}{A}\right)_I} = \frac{\rho_{eI}(x)}{N_a\left(\frac{Z}{A}\right)_I} = \rho_I(x);$$

Aside from the above special case, $a_I(x)$ is not the same as $\rho_I(x)$. That is, whenever a voxel contains a material other than water and iodine, such as even a lipid or collagen, which have effective atomic numbers different from those of the basis materials, its contribution to the x-ray attenuation will be assigned to material basis images. In this case, the assumption that $a_I(x)$ is same as $\rho_I(x)$ will inevitably lead to either over- or under-estimation of the PBV. Thus, even when espousing that "traditional," non-multi-facet or non-multi-energy/polychromatic CT datasets or images were used to calculate PBV, this is clinically inaccurate and reflective of a misnomer. At best, if anything other than water and iodine is in the VOI used to calculate PBV, the result is rPBV and not PBV, regardless of what the calculation asserts.

Thus, the present disclosure provides a way to actually determine PBV, even in voxels containing materials other than water and iodine, which is a clinical reality and necessity. The present disclosure recognizes that, the $Z_{eff}$ formula in Equation (12) can be recast:

$$Z_{eff}^\beta = f_I Z_I^\beta + \Sigma_{j=2}^n f_j Z_j^\beta \tag{14};$$

where $f_i$ (j=2, ... n) denotes the electron fraction for non-iodine materials in the VOI. Since different VOIs have different compositions characterized by $f_j$ and $Z_j$, these quantities and the consequently derived quantity $Z_{eff}$ in Eq. (14) should be interpreted at VOI dependent quantifies and we use the center location of the VOI, x, to denote this spatial dependence. As shown in Table 1, the atomic numbers of non-iodine materials in the lung are similar to $Z_w$ and are much smaller than $Z_I$.

TABLE 1

| Material | Air (dry) | Pulmonary tissue | Adipose tissue | Water | Muscle | Iodine |
|---|---|---|---|---|---|---|
| $Z_{eff}$ | 7.66 | 7.44 [7.34, 7.46] | 5.82 [5.69, 5.90] | 7.42 [7.31, 7.46] | 7.52 [7.42, 7.52] | 53 |
| Density (g/ml) | $1.2 \times 10^{-3}$ | 1.05 | 0.95 | 1.0 | 1.05 | 4.9 |
| Electron density (mol/ml) | $6.0 \times 10^{-4}$ | 0.58 | 0.53 | 0.56 | 0.58 | 2.05 |

As a result, the following approximation can be justified:

$$Z_{eff}^\beta \approx f_I Z_I^\beta + Z_w^\beta \Sigma_{j=2}^n f_j = f_I Z_I^\beta + Z_w^\beta(1 - f_I) \tag{15};$$

Therefore:

$$f_I(x) \approx \frac{Z^\beta_{eff}(x) - Z^\beta_w}{Z^\beta_I - Z^\beta_w}; \tag{16}$$

Per the definition of electron fraction, $f_I(x)$ can be written as:

$$f_I = \frac{\left(\frac{Z}{A}\right)_I fm_I}{\sum\left(\frac{Z}{A}\right)_j fm_j} \approx \frac{\frac{1}{2} fm_I}{\frac{1}{2}\sum_j fm_j} \approx \frac{m_I}{m_{lung}} = \frac{m_I}{\rho_{lung} V_{lung}}; \tag{17}$$

where the above is informed by the fact that for the majority of tissue materials, $$\frac{Z}{A} \approx \frac{1}{2}.$$

Based on both Equations (16) and (17):

$$\frac{m_I(x)}{\rho_{lung}(x) V_{lung}(x)} \approx \frac{Z_{eff}^\beta(x) - Z_w^\beta}{Z_I^\beta - Z_w^\beta}. \quad (18)$$

The mass of iodine in the VOI, $m_I(x)$, is related to $V_{cap}(x)$ and $\rho_{I_o}$ by:

$$V_{cap}(x) = \frac{m_I(x)}{\rho_{I_0}}; \quad (19)$$

According to Equations (18) and (19) and the PBV formula in (2):

$$PBV(x) = \frac{\frac{m_I(x)}{\rho_{I_0}}}{\rho_{lung} V_{lung}} \approx \frac{1}{\rho_{I_0}} \frac{Z_{eff}^\beta(x) - Z_w^\beta}{Z_I^\beta - Z_w^\beta}. \quad (20)$$

As will be explained, this formulation of PBV can be used for the absolute quantification of PBV using multi-faceted CT datasets or images. As noted above, this stands in stark contrast to the rPBV that is determined when traditional or conventional CT data or images (non-multi-faceted CT datasets or images) are used to determine "PBV."

The first reason for this distinction, as explained above, is that the iodine basis image, $a_I(x)$, is not the same as the iodine concentration distribution, $\rho_I(x)$, despite the fact that the physical unit of $a_I(x)$ is the same as that of $\rho_I(x)$ (e.g., mg/ml). Second, compared with the PBV formula in Equation (7), using $a_I$ as a surrogate for the rPBV ignores the dependence of the PBV on the lung tissue density $\rho_{lung}(x)$, a quantity that varies spatially in the lung.

Figure 6C:
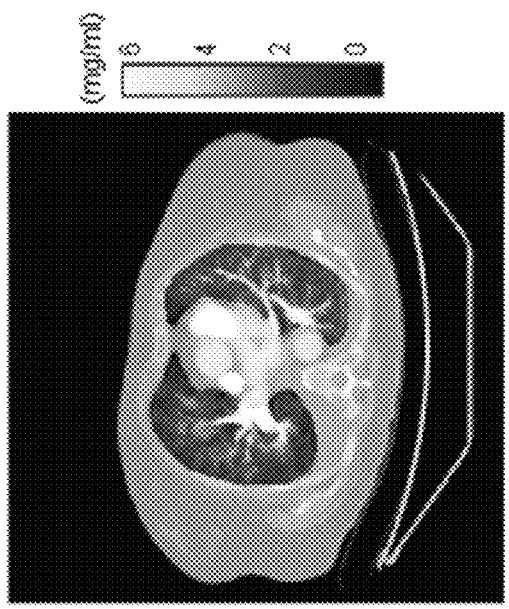
FIG. 6C is a iodine basis image from the patient illustrated in FIG. 6A.
Figure 6B:
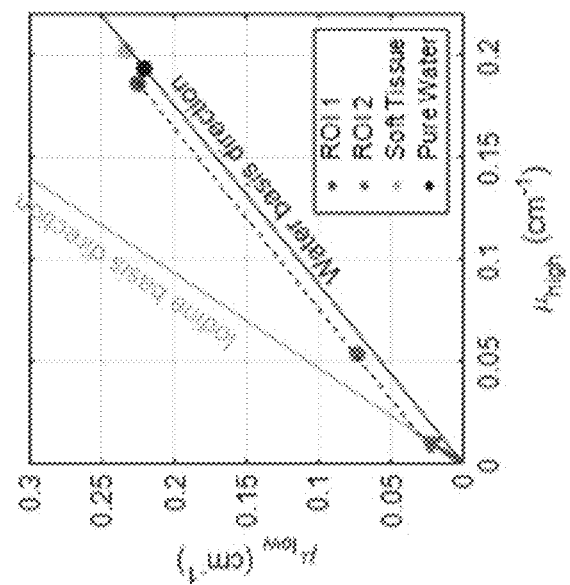
FIG. 6B is a graph showing that, for each ROI, its signal in the iodine basis image is given by projecting ($\mu$_low, $\mu$_high).
Figure 6A:
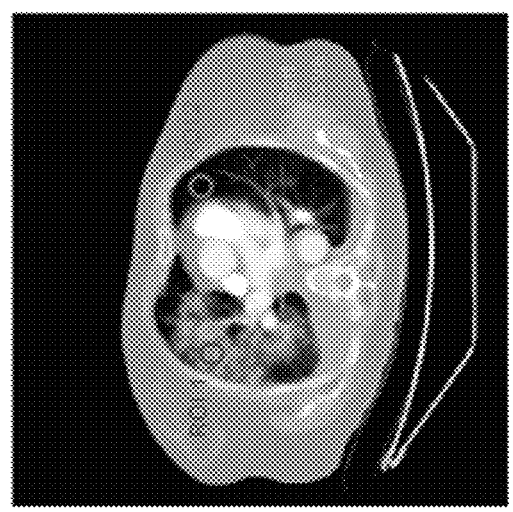
FIG. 6A is a 140 kV CT image of a patient showing multiple volumes of interest.

Referring to FIGS. 6A-6C, when a local lung region contains a consolidation or excess interstitial fluid, its density can be much higher than the density of normal lung parenchyma. As a result, the use of $a_I(x)$ can severely overestimate the PBV in the consolidated region. Specifically, FIG. 6A is a 140 kV CT image of a patient showing consolidation in the right lung. Three regions-of-interest (ROIs) are drawn on the consolidation, the contralateral lung, and a soft tissue region. Referring to FIG. 6B, for each ROI in FIG. 6B, the mean attenuation coefficient measured in the 80 kV image ($\mu_{low}$) was plotted against the attenuation coefficient measured in the 140 kV image ($\mu_{high}$) in FIG. 6B. For each ROI, its signal in the iodine basis image is given by projecting ($\mu_{low}, \mu_{high}$) towards the iodine basis direction along the dashed black line that is parallel to the water basis direction. The consolidation region yielded the same iodine basis signal due to its much higher density. In FIG. 6C, the iodine basis image of the same patient is provided. The consolidation region and the healthy lung region have the same signal in the iodine basis image.

Due to the above two pitfalls—(1) the iodine basis image, $a_I(x)$, is not the same as the iodine concentration distribution, $\rho_I(x)$ and (2) using $a_I$ as a surrogate for the rPBV ignores the dependence of the PBV on the lung tissue density $\rho_{lung}(x)$, a quantity that varies spatially in the lung—in the rPBV estimations, the iodine basis image alone cannot be used to assess pulmonary function. That is attempting to use the iodine basis image alone does not provide the sensitivity and specificity needed for clinical applications, as a higher $a_I$ value does not necessarily mean a higher perfused blood volume, and a "normal" $a_I$ value does not necessarily rule out perfusion defects.

Thus, a true or absolute quantification of PBV—not rPBV masquerading as actual PBV—is needed, which the systems and methods provided herein achieve. Instead of using the iodine basis image as a relative measure of the PBV, the present disclosure provides a new metric that provides a quantitative or absolute measure PBV. As shown above, the PBV defined in Equation (7) is quantitatively related to the effective atomic number $Z_{eff}$ as follows:

$$PBV(x) = aZ_{eff}^\beta(x) + b \quad (21);$$

where constants a and b are determined as follows:

$$a = \frac{1}{\rho_{I_0}(Z_I^\beta - Z_w^\beta)}, \; b = -\frac{Z_w^\beta}{\rho_{I_0}(Z_I^\beta - Z_w^\beta)}. \quad (22)$$

The value of the exponent $\beta = 2.94$ can be derived empirically, as demonstrated in general literature on the effective atomic number and energy absorption in various tissues. Since both $Z_{eff}(x)$ and $\rho_{I_o}$ can be directly provided by multi-faceted CT acquisitions, Equation (21) provides an absolute (rather than relative) measurement of PBV with a physical unit of ml/g or ml/100 g depending on the user's preference. As shown in Table 1, $Z_{eff}$ of iodine is almost an order of magnitude higher than those of other materials commonly appearing in the lung. Therefore, an additional theoretical advantage of proposed PBV measurement method is its much higher sensitivity to iodine concentration.

Figure 7:
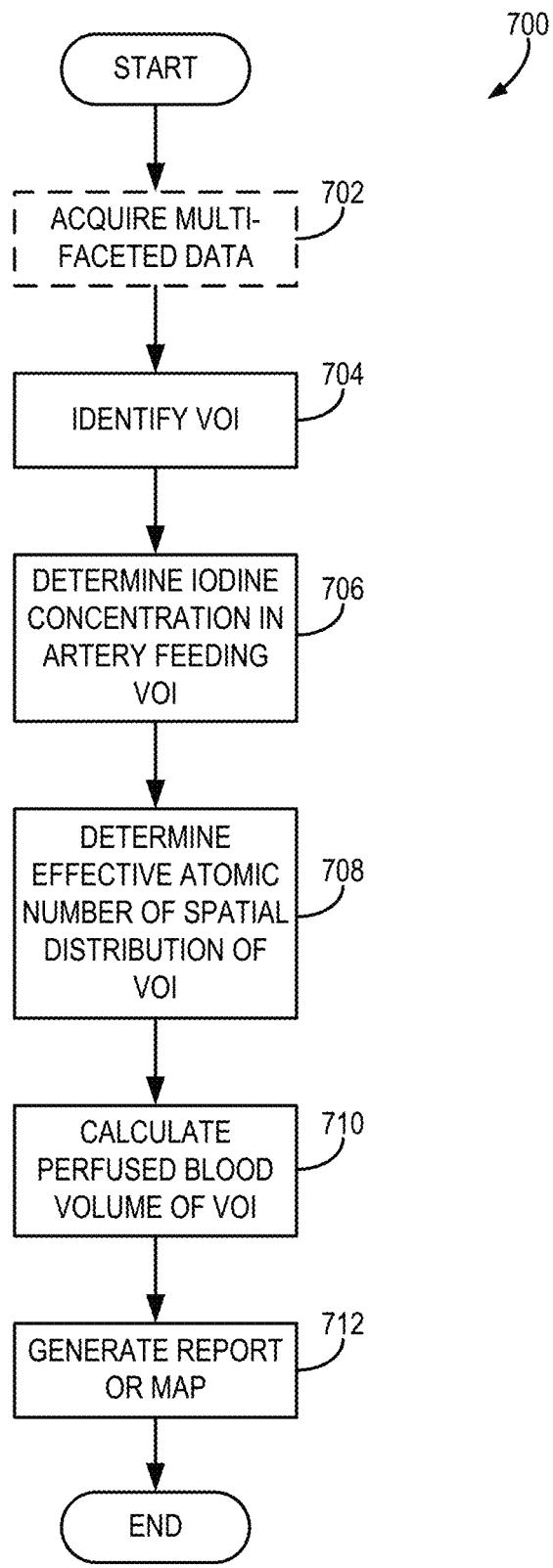
FIG. 7 is a flow chart setting forth steps of an example of a method in accordance with the present invention.

Referring now to FIG. 7, a flow chart is provided setting forth the steps of one, non-limiting example of a clinical workflow in accordance with the present disclosure. At process block 702, as described above, multi-faceted CT data is acquired. As shown in FIG. 7, this step may be optional because, as further described, the systems and methods may be applied to newly-acquired data or images or may be applied to stored or previously-acquired data. Regardless of when or how the multi-faceted CT data were acquired, at process block 704, one or more VOI is identified in the subject. For each identified VOL at process block 706, the iodine concentration in the artery feeding the VOI is determined (i.e., $\rho_{I_o}$) is determined. Also, at process block 708, the effective atomic number of the spatial distribution of the VOI (i.e., $Z_{eff}$) is determined. Again, as described above, absolute or quantitative perfused blood volume (PBV) is quantitatively related to the effective atomic number $Z_{eff}$ as PBV(x)=a $Z_{eff}^\beta(x)$+b, where constants a and b are determined as $$a = \frac{1}{\rho_{I_0}(Z_I^\beta - Z_w^\beta)} \text{ and } b = -\frac{Z_w^\beta}{\rho_{I_0}(Z_I^\beta - Z_w^\beta)}.$$

The value of the exponent $\beta = 2.94$. Therefore, once $Z_{eff}(x)$ and $\rho_{I_o}$ are derived at process blocks 704 and 706, one can determine an absolute or quantitative (rather than relative)

measurement of PBV with a physical unit of [ml/g] or [ml/100 g] depending on the user's preference, at process block 710. At process block 712, a report of PBV, an image showing PBV over the VOI(s), and/or a map can be generated. This can be done in an automated fashion, such as via a processor, such as described above, using artificial intelligence (AI) or machine learning (ML), or a combination of these and other resources.

EXAMPLES

The above-described process was utilized with patients to assess clinical information. In one study, pulmonary DECT angiography data acquired from 4 human subjects were retrospectively collected and processed under IRB approval. Among these subjects, three received DECT on a 256-slice MDCT scanner (Revolution CT, GE Healthcare) equipped with the GSI DECT technology and one subject received DECT on a 64-slice MDCT scanner (GE Discovery CT750 HD) equipped with GSI. The other salient information is included in Table 2.

TABLE 2

|  | Subject 1 | Subject 2 | Subject 3 | Subject 4 |
| --- | --- | --- | --- | --- |
| Age | 40 | 65 | 68 | 23 |
| BMI | 26.9 | 36.9 | 27.4 | 20.4 |
| Gender | male | female | male | female |
| Scanner | 750HD | Revolution | Revolution | Revolution |
| Contrast volume | 100 ml | 100 ml | 100 ml | 100 ml |
| Contrast type | Isovue370 | Omnipaque300 | Omnipaque300 | Omnipaque300 |
| Helical pitch | 1.375 | 0.992 | 0.992 | 0.992 |
| Beam Collimation | 40 mm | 80 mm | 80 mm | 80 mm |
| Rotation time | 0.5 | 0.5 | 0.5 | 0.5 |
| mA | 600 | 240 | 200 | 200 |

For scans performed on the 256-slice CT system, the intravenous contrast injection used 100 ml of Iohexol 300 mgI/ml (Omnipaque 300, GE Healthcare) with a 10 ml saline flush, both at a rate of 5 ml/s. A bolus tracking scan (SmartPrep, GE Healthcare) was used to determine the scan timing. Once the enhancement in the left atrium exceeded 60 HU, the actual DECT angiography scan was triggered and performed under the helical mode with a helical pitch of 0.992. The scan range extended from the apices of the lung to just below the diaphragm. The x-ray tube potential rapidly switched between 80 and 140 kV while the gantry rotated at a speed of 0.5 s per revolution. The tube current (mA) was adjusted for each subject based on their body size under the guidance of the GSI-Assist technology. The beam collimation was 80 mm and the reconstruction slice thickness was 1.25 mm. For the subject who received the DECT on the 64-slice scanner, the contrast injection was 100 ml of Iopamidol 370 mgI/ml (Isovue 370, Bracco Diagnostics Inc.) at a rate of 4 ml/s, followed by 45 ml of saline at 2 ml/s. The bolus tracking scan used a region-of-interest (ROI) placed on the pulmonary artery at the level of carina, and the trigger threshold was 110 HU.

For each subject, iodine and water basis images and effective atomic number maps were generated from the DECT acquisition. The iodine concentration of the feeding artery, $\rho_{I_o}$, was measured by placing an ROI on the pulmonary trunk in the iodine basis image. Equation (10) was then used to calculate the PBV from the measured $Z_{eff}$ and $\rho_{I_o}$ and the known values of $Z_w$ and $Z_I$. The PBV maps were color-coded using the "hot" color map and overlaid on the grayscale 140 kV-equivalent (QC) CT images.

A radiologist with 35 years of clinical experience evaluated both $Z_{eff}$-based absolute PBV maps and iodine image-based relative PBV maps. For each patient and each type of PBV map, the reader evaluated whether the images demonstrated evidence of perfusion defects, ground-glass opacities (GGO), consolidations, atelectasis, lung tumors, or other pulmonary abnormalities. The gold-standard diagnosis was established based on clinical and laboratory records, CT and nuclear medicine images (if available), and other relevant imaging results. The diagnostic performance of absolute and relative PBVs were compared qualitatively by the experienced radiologist.

Figure 8:
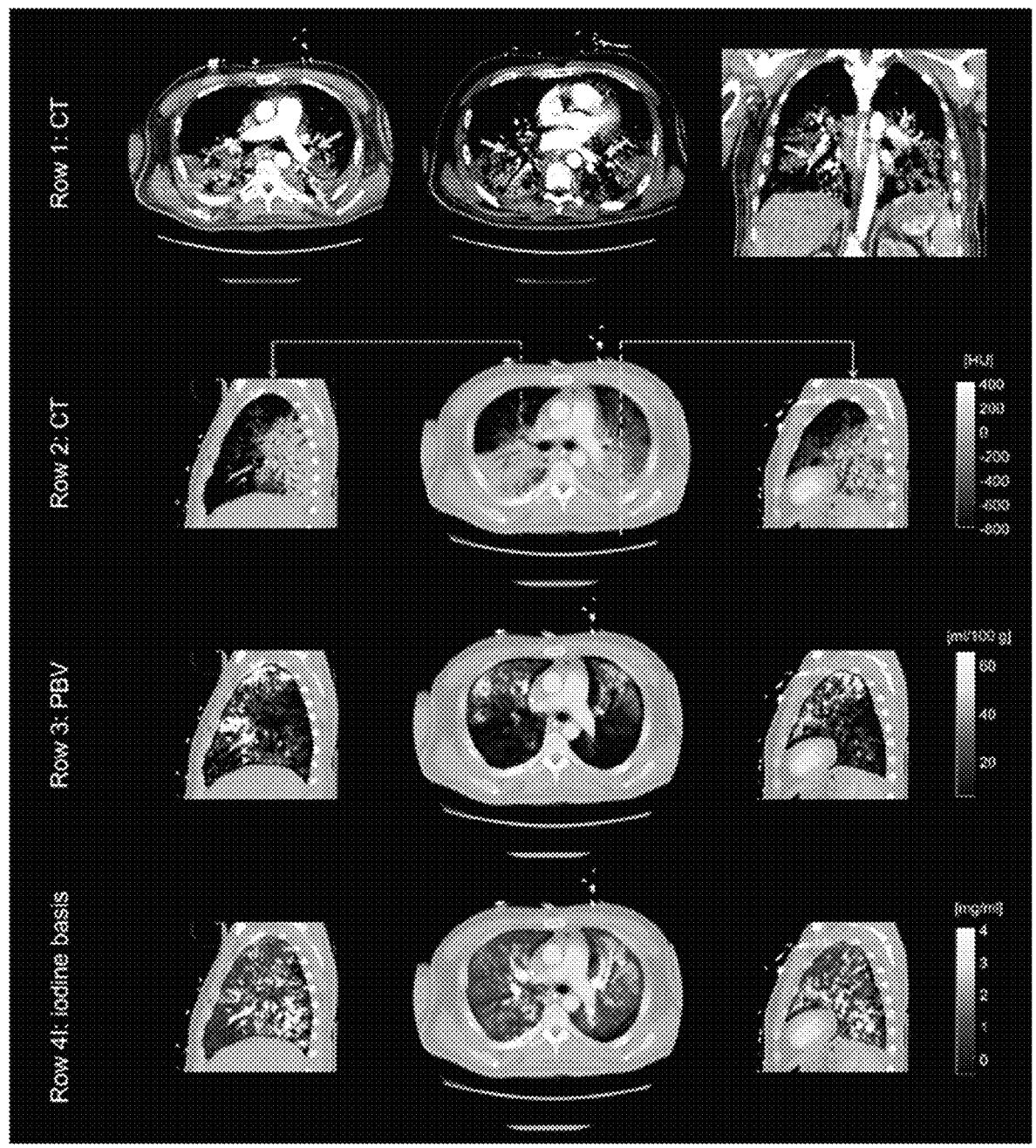
FIG. 8 is a set of correlated images of a subject with clinically proven pneumonia and acute pulmonary embolism.

In particular, FIG. 8 provides a set of images of Subject 1 with clinically confirmed acute PE and pneumonia. Extensive ground glass opacity (GGO) and consolidation were found in the posterior regions of both lungs. As shown by the same subject's pulmonary CTA images in the first row of FIG. 8, multiple emboli exist in the pulmonary vessels supplying the posterior lung regions. The PBV maps demonstrate regional perfusion defects in the lungs. In comparison, the iodine basis images do not clearly show the perfusion defects. This is because the consolidation and GGO elevated the local mass density of the lung which increased the signal of the consolidated lung tissues in the iodine basis images and counteracted the reduction of blood perfusion in those areas.

Figure 9:
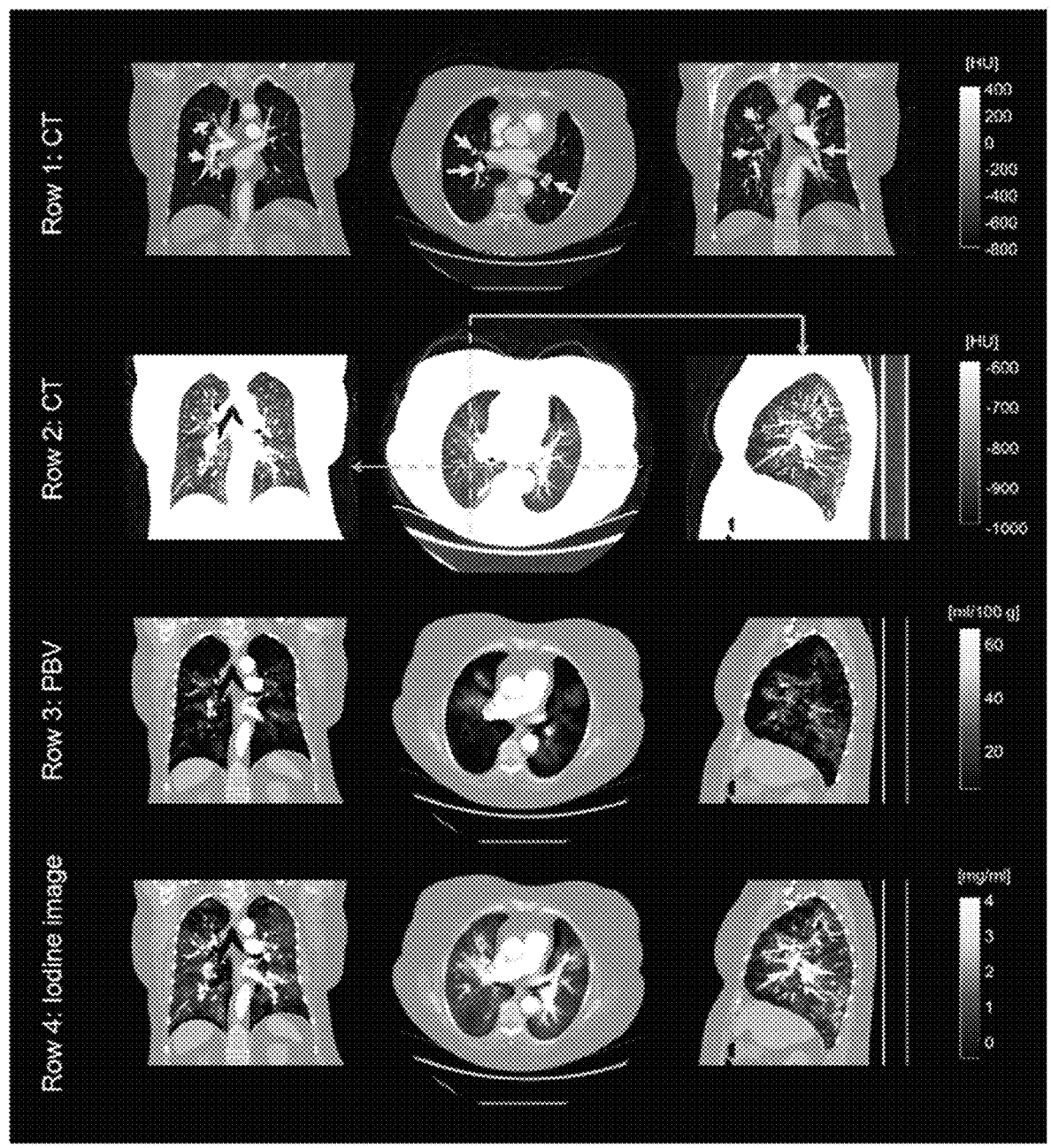
FIG. 9 is a set of correlated images of a subject with clinically confirmed pulmonary embolism.

Continuing, FIG. 9 shows images of Subject 2 with clinically confirmed PE. The subject has a history of lung infection and consolidations and GGOs within the bilateral upper and right middle lobes. The bilateral lobar, segmental and subsegmental pulmonary emboli can be seen on the pulmonary CTA images in the first row in FIG. 9. The PBV maps show a global reduction in blood volume. Some regions, such as the bilateral upper lobes, show severe perfusion defects. Although the iodine basis images also show regional defects in the upper lobes, it failed to show the systematic reduction in blood perfusion because it is a relative instead of an absolute quantity (its value is related to the global iodine concentration level as well as local lung tissue density). The GGOs might have slightly increased the local pulmonary tissue density and reduced the sensitivity of the iodine basis image to perfusion defects.

Figure 10:
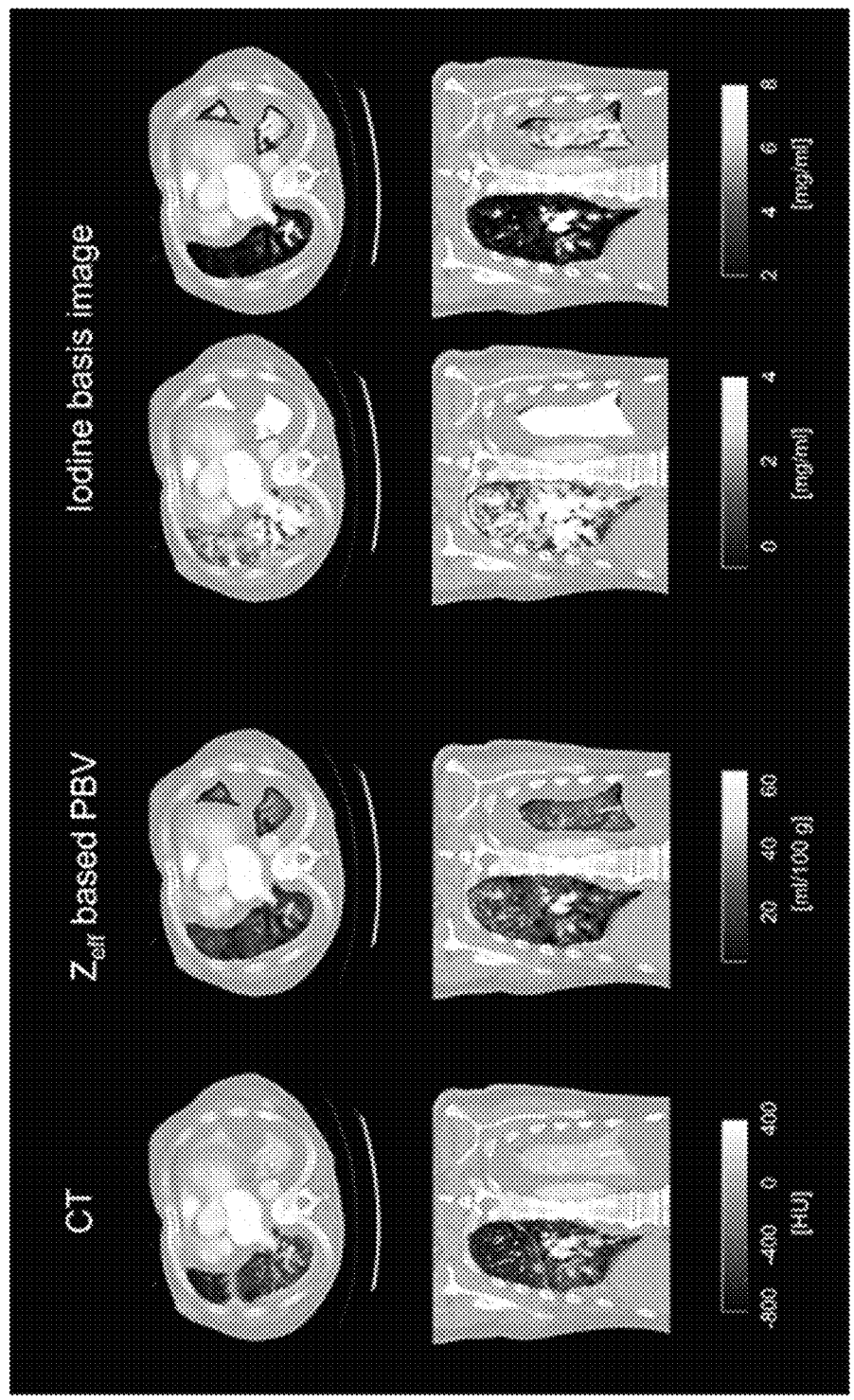
FIG. 10 is a set of correlated images of a subject without any pulmonary embolism or pulmonary hypertension.

Referring now to FIG. 10, images of Subject 3 who has left and pericardial pleural effusions and compressive collapse of the left lower lobe with atelectasis in the left lung are shown. However, no PE or pulmonary hypertension was found in the patient. The PBV maps show normal perfusion with an average PBV value of 29±5 ml/100 g in the left lung and 25±7 mg/100 g in the right lung. In comparison, the iodine basis images of this subject show a much higher signal in the left lung (6.6±1.3 mg/ml) than the right lung (2.8±1.5 mg/ml). Instead of a greater blood perfusion, the high iodine basis signal of the left lung was actually caused by the excessive fluid that significantly increased the mass density of the area. If a sub-optimal display range is used for the iodine basis image (4$^{th}$ column in FIG. 10), the right lung may appear hypoperfused compared with the left lung. This example shows a limitation of the iodine basis image-based relative perfusion measurement and an advantage of the proposed quantitative PBV measurement.

Figure 11:
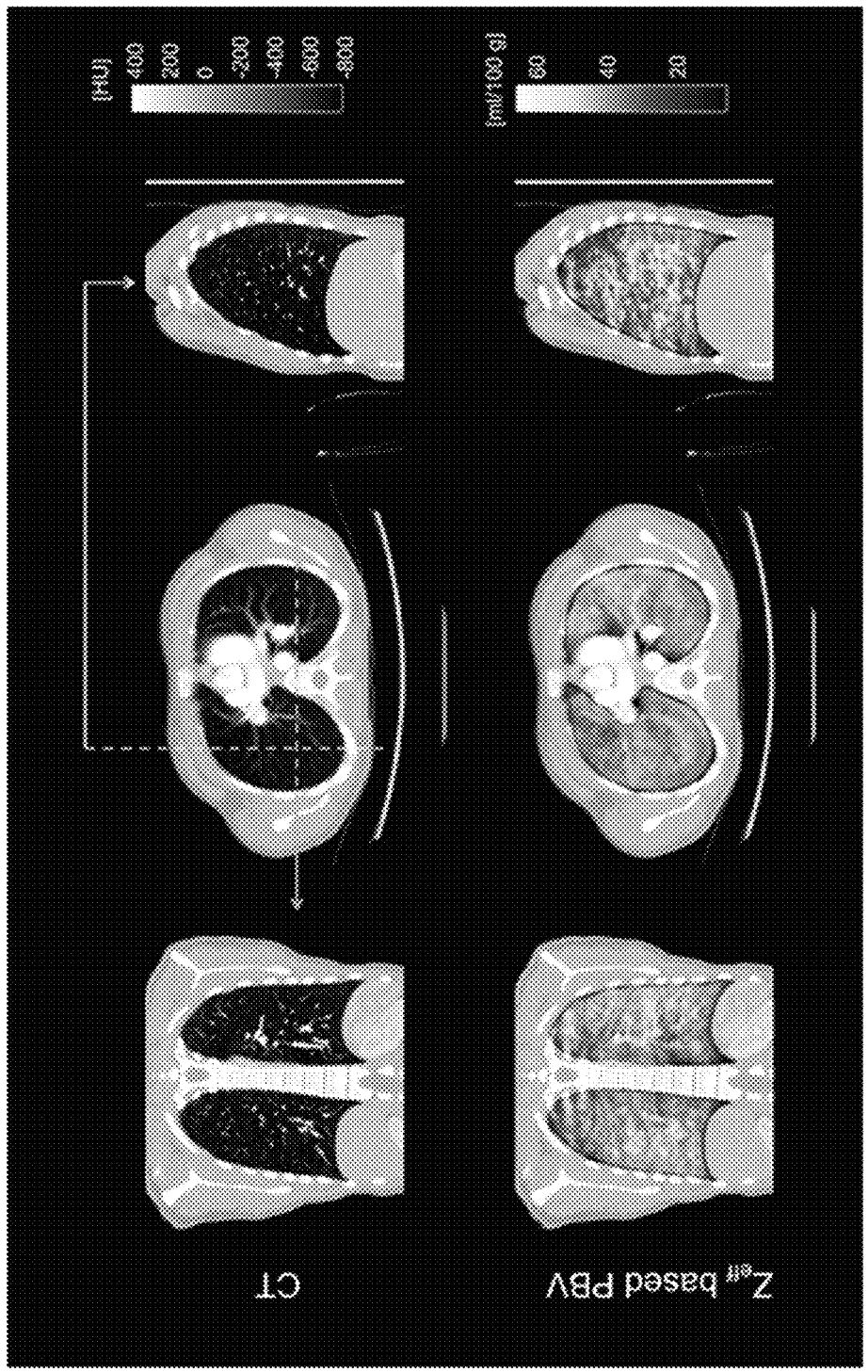
FIG. 11 is a set of correlated images of a subject without pulmonary embolism and without pulmonary hypertension.

Finally, FIG. 11 provides a set of images of a "control" case (Subject 4) for whom the clinical record has ruled out PE or other lung diseases. The PBV maps show homogenous and normal pulmonary perfusion signals without any false perfusion defects. The average PBV value is 40 ml/100 g.

In existing commercial DECT systems, pulmonary perfusion conditions are estimated using iodine basis images generated by applying a three-material (e.g., iodine, air, soft tissue) or two-material decomposition to the acquired dual-energy CT data. There are two fundamental pitfalls of this approach.

First, as shown with respect to Equation 10 a material with an effective atomic number different from those of the basis materials can be partially assigned to the iodine basis images. Therefore, the iodine basis images are not equal to the iodine density distribution, $\rho_I(\vec{x})$. This difference can be significant for targeted lung regions in which there exist differences between soft tissue and the basis material used in the material decomposition process. The typical clinical conditions that could result in incorrect partial assignment for a given material include consolidations and ground glass opacities (Subjects 1 and 2), atelectasis (Subject 3), or other high-density tissues.

Second, by definition, PBV is the volume of blood perfused in a unit mass of lung tissue, as described by Equation 1. The iodine basis images do not directly measure the volume of blood, nor do they directly reflect the mass of the lung tissue in a given image voxel. One can argue that image voxel values, with a unit of [mg of iodine per ml], have a positive correlation with iodine density and thus has a positive correlation with PBV according to Equation 7. However, the existence of a positive correlation does not necessarily indicate the iodine basis images are quantitatively related to the PBV maps due to the fact that an important quantity, $\rho_{lung}(x)$, in the PBV formula in Equation 7 is not characterized by the iodine basis images.

Therefore, at best, the identification of perfusion defects in iodine basis images typically relies heavily on the choice of display window/level, the choice of display color map, the relative difference in color between different lung regions, and the reader's experience. In stark contrast, the systems and methods of the present disclosure show that a quantitative or absolute measurement of PBV can be determined by the effective atomic numbers measured from multi-facet (dual- or multi-energy CT data or polychromatic CT data) to yield a quantitative biomarker.

As shown by the preliminary human subject results presented above, for patients with acute PE and pneumonia, the absolute or quantitative PBV maps clearly demonstrate regional perfusion defects in the area supplied by the embolized vessels, while the iodine basis images failed to demonstrate the defects since pneumonia-induced consolidation elevated local tissue density and counteracted the reduced perfusion in the area. Furthermore, for a patient without PE, but with pleural effusion and atelectasis, the quantitative or absolute PBV maps correctly demonstrate normal perfusion and are more specific than iodine image-based relative perfusion maps.

In addition, the above-described absolute or quantitative PBV information can be combined with other information, such as hemodynamic information, including pulmonary blood flow (PBF). If one desires to obtain a complete set of perfusion measurements including pulmonary flow information, instead of or in addition to data for steady-state perfusion measurements, time-resolved CT scans can be performed to measure the contrast dynamics of pulmonary vasculature and tissues.

In clinical practice, the systems and methods provided herein can be used to identify or search for blood clots, or assist with or estimate a prognosis, such as in pneumonia. Furthermore, the systems and methods provided herein can be used in other clinical applications, such as cancer analysis or prognosis, including when identifying or searching for a mass, such as a lung mass, or fibrosis and other diagnoses, separate from lung density and perfusion.

Thus, a quantitative biomarker from multi-faceted CT imaging is provided that can be used to quantitatively assess pulmonary perfusion blood volume (PBV). Different from the traditional iodine image-based relative pulmonary perfusion measurements, the systems and methods provided herein show that quantitative or absolute PBV can be provided using effective atomic number images generated from multi-faceted acquisitions and, thus, the derived PBV provides a robust and quantitative characterization of potential pulmonary perfusion defects.

In addition, the above described methods can be applied to multi-energy or polychromatic datasets or images that were even acquired prior to the creation of the systems and methods provided herein. That is, the systems and methods provided herein can be used as "post-processing" or retrospectively process previously-acquired multi-energy or polychromatic datasets to yield quantitative or absolute PBV maps. Thus, the systems and methods provided herein can be realized on a full CT scanning system, such as described above, or on a workstation or other computing device. Furthermore, though the above-described examples described pulmonary examples, the systems and methods provided herein are not limited to any particular clinical application. For example, the systems and methods provided herein can be utilized in variety of clinical application, such as cerebral perfusion or renal perfusion, in addition to lung perfusion, to name just a few.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for determining perfusion blood volume from computed tomography (CT) data acquired from a subject, the system comprising:
    a storage medium having multi-faceted CT data stored thereon that includes data acquired with at least one of a multi-energy x-ray source or a polychromatic x-ray source;
    a computer system configured to:
        receive the multi-faceted CT data from the storage medium;
        derive an iodine concentration in an artery feeding a volume of interest (VOI) in the multi-faceted CT data;

determine an effective atomic number of a spatial distribution in the VOI;

calculate a perfused blood volume of the VOI using the iodine concentration and the effective atomic number;

generate a report of the perfused blood volume of the VOI; and a display configured to display the report, including the perfused blood volume of the VOI.

2. The system of claim 1 wherein the computer system is configured to calculate the perfused blood volume using an energy- and material-independent numerical constant.

3. The system of claim 2 wherein the energy- and material-independent numerical constant has a value of approximately 3.

4. The system of claim 2 wherein energy- and material-independent numerical constant has a value of 2.94.

5. The system of claim 1 wherein the computer is further configured to calculate the perfused blood volume as:

PBV(x)=a $Z_{eff}^{\beta}$(x)+b, where constants a and b are determined as $$a = \frac{1}{\rho_{I_0}(Z_I^{\beta} - Z_w^{\beta})} \text{ and } b = -\frac{Z_w^{\beta}}{\rho_{I_0}(Z_I^{\beta} - Z_w^{\beta})},$$

and wherein $Z_{eff}$ is effective atomic number of a spatial distribution in the VOI, $\rho_{I_o}$ is the iodine concentration in the artery feeding the VOI, $Z_I$ and $Z_w$ are the atomic numbers of pure iodine and water, respectively, and $\beta$ is an energy- and material-independent numerical constant.

6. The system of claim 1 wherein the storage medium is part of a CT system configured to acquire the multi-faceted CT data and the computer processor is part of a workstation.

7. The system of claim 1 wherein the computer processor is configured to reconstruct the multi-faceted CT data into effective atomic number images and determine the iodine concentration and the effective atomic number form the effective atomic number images.

8. The system of claim 7 wherein the computer processor is further configured to determine the perfused blood volume as PBV(x)=a $Z_{eff}^{\beta}$(x)+b, where a, b, and $\beta$ are constants and $Z_{eff}$ is effective atomic number of a spatial distribution.

9. A method for generating reports on perfusion blood volume from computed tomography (CT) data acquired from a subject, the method comprising:

receiving multi-faceted CT data acquired from the subject using one of a multi-energy or polychromatic CT acquisition;

deriving an iodine concentration in an artery feeding an volume of interest (VOI) in the multi-faceted CT data;

determining an effective atomic number of a spatial distribution in the VOI;

calculating a perfused blood volume of the VOI using the iodine concentration and the effective atomic number;

generating a report of the perfused blood volume of the VOI.

10. The method of claim 9 further comprising controlling a CT system to perform the one of a multi-energy or polychromatic CT acquisition.

11. The method of claim 9 further comprising calculating the perfused blood volume using an energy- and material-independent numerical constant.

12. The method of claim 11 wherein the energy- and material-independent numerical constant has a value of approximately 3.

13. The method of claim 11 wherein energy- and material-independent numerical constant has a value of 2.94.

14. The method of claim 9 wherein calculating the perfused blood volume includes using:

PBV(x)=a $Z_{eff}^{\beta}$(x)+b, where constants a and b are determined as $$a = \frac{1}{\rho_{I_0}(Z_I^{\beta} - Z_w^{\beta})} \text{ and } b = -\frac{Z_w^{\beta}}{\rho_{I_0}(Z_I^{\beta} - Z_w^{\beta})},$$

and wherein $Z_{eff}$ is effective atomic number of a spatial distribution in the VOI, $\rho_{I_o}$ is the iodine concentration in the artery feeding the VOI, $Z_I$ and $Z_w$ are the atomic numbers of pure iodine and water, respectively, and $\beta$ is an energy- and material-independent numerical constant.

15. The method of claim 9 further comprising reconstructing the multi-faceted CT data into effective atomic number images and determine the iodine concentration and the effective atomic number form the effective atomic number images.

16. The method of claim 15 wherein determining the perfused blood volume includes using PBV(x)=a $Z_{eff}^{\beta}$(x)+b, where a, b, and $\beta$ are constants and $Z_{eff}$ is effective atomic number of a spatial distribution.

* * * * *

UNITED STATES PATENT AND TRADEMARK OFFICE
CERTIFICATE OF CORRECTION

PATENT NO. : 11,826,190 B2
APPLICATION NO. : 17/375549
DATED : November 28, 2023
INVENTOR(S) : Guang-Hong Chen et al.

It is certified that error appears in the above-identified patent and that said Letters Patent is hereby corrected as shown below:

On the Title Page

Abstract, "VOL calculating" should be --VOI calculating--.

In the Specification

Column 1, Line 9, "EB021183 and EB020521" should be --EB021183--.

Column 12, Line 50, "VOL" should be --VOI--.

Signed and Sealed this
Third Day of September, 2024

Katherine Kelly Vidal
*Director of the United States Patent and Trademark Office*